United States Patent [19]

LLinas et al.

[11] Patent Number: 4,677,982

[45] Date of Patent: Jul. 7, 1987

[54] INFRARED TRANSCUTANEOUS COMMUNICATOR AND OF METHOD USING SAME

[75] Inventors: Rodolfo R. LLinas; Mutsuyuki Sugimori; Ronald K. Crank, all of New York, N.Y.

[73] Assignee: New York University, New York, N.Y.

[21] Appl. No.: 594,990

[22] Filed: Mar. 29, 1984

Related U.S. Application Data

[63] Continuation-in-part of Ser. No. 336,337, Dec. 31, 1981, abandoned.

[51] Int. Cl.⁴ ................................................ A61B 5/00
[52] U.S. Cl. .................................... 128/664; 340/573; 340/870.28
[58] Field of Search .......... 128/664, 665, 642, 419 PT, 128/419 P, 419 PG, 419 R, 696, 697, 903, 908, 736; 604/153; 340/870.28, 870.29, 573

[56] References Cited

U.S. PATENT DOCUMENTS

| | | | |
|---|---|---|---|
| 3,527,220 | 9/1970 | Summers | 604/153 |
| 3,672,352 | 6/1972 | Summers | 128/664 X |
| 3,945,387 | 3/1976 | Adams | 128/419 PG |
| 4,041,954 | 8/1977 | Ohara | 128/697 |
| 4,187,854 | 2/1980 | Hepp et al. | 128/419 PT |
| 4,223,679 | 9/1980 | Schulman et al. | 128/419 PT |

OTHER PUBLICATIONS

Kadefors, "Controlled . . . Biotelemetry Devices", IEEE Trans. Bio. Eng., vol. 23, No. 2, Mar. 1976, pp. 124–129.
Ko et al, "RF-Powered . . . Biotelemetry", IEEE Trans. Bio. Eng., vol. 27, No. 8, Aug. 1980, pp. 460–467.
Claude et al, "A Chronically . . . Research", IEEE Conf., Denver, Colo., 1979, pp. 334–336.
Klein et al, "An Eight Channel . . . Medium", IEBB 1979 Conference, Denver, Colo., 6–7 Oct. 1979, pp. 273–275.

*Primary Examiner*—Lee S. Cohen
*Attorney, Agent, or Firm*—Spencer & Frank

[57] ABSTRACT

A method and apparatus are disclosed for transcutaneous communication using infrared light signals to communicate bidirectionally between electronic apparatus implanted within a living organism and electronic apparatus external to the body by which measurements of physiological data can be obtained and command signals can be imposed on implanted apparatus.

7 Claims, 1 Drawing Figure

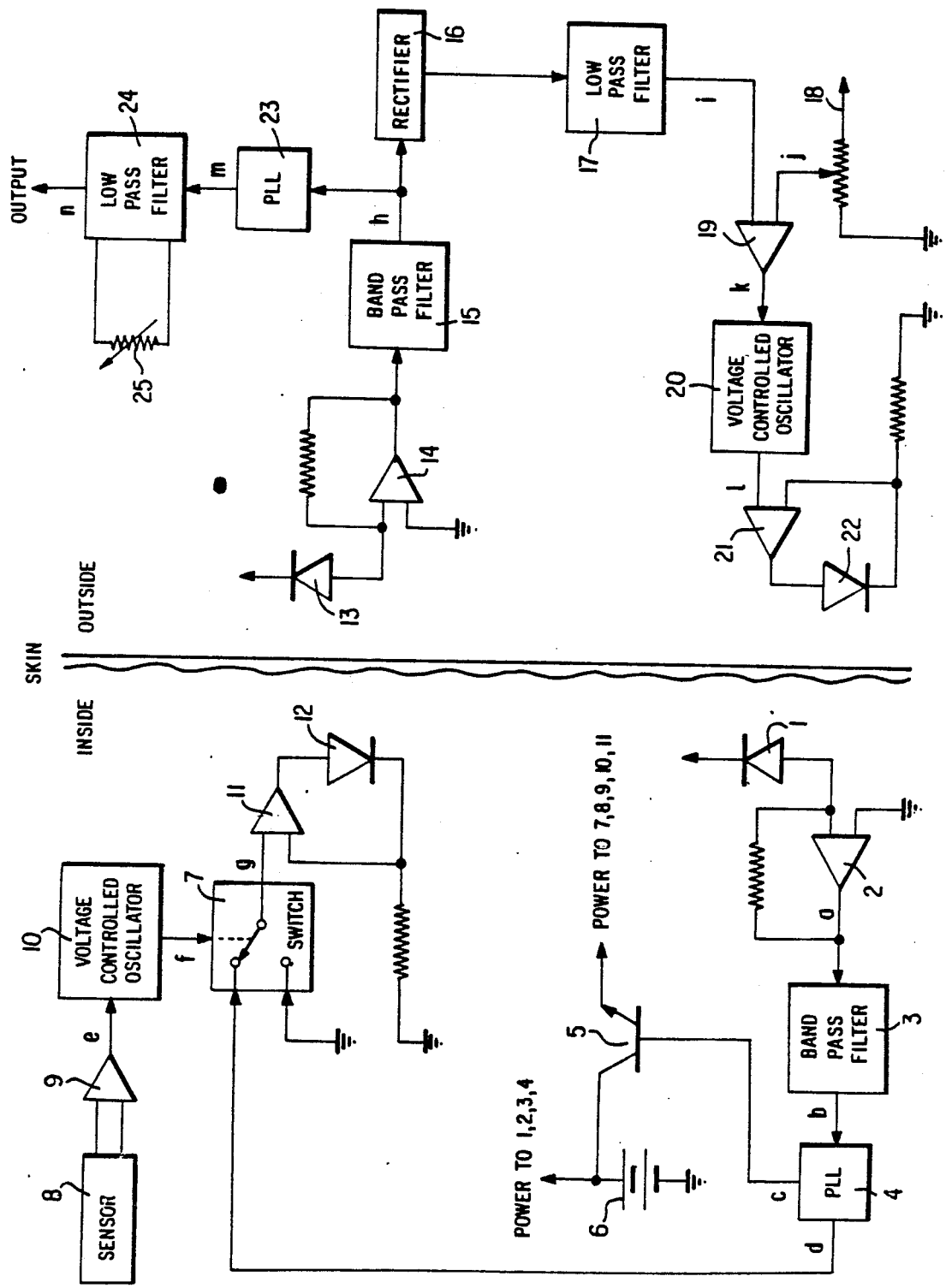

INFRARED TRANSCUTANEOUS COMMUNICATOR AND METHOD OF USING SAME

CROSS-REFERENCE TO RELATED APPLICATION

This is a continuation-in-part of application Ser. No. 336,337, filed Dec. 31, 1981, and now abandoned.

FIELD OF THE INVENTION

The invention pertains to a method and apparatus which minimize the power requirements for transcutaneous communication. Infrared light signals are used to control the bidirectional transfer of information between electronic apparatus implanted beneath the skin of a living organism and other apparatus which is located externally. Physiological and biochemical data can be measured and transmitted through the skin to the external apparatus.

BACKGROUND OF THE INVENTION

A primary concern with any electronic device intended for implantation within the body is its power consumption as the power requirements dictate the ultimate size and operational lifetime of an implant. Most devices are powered by batteries that must be replaced to restore power, and surgical removal always involves risk and inconvenience to the patient. This undesirable feature greatly detracts from the benefits which may be gained from an implant device.

Transcutaneous transmission of information requires that the transmitter power be minimized. Over a period of time, fibrotic tissue may increase the density of the dermal cover and affect transmitted signal power requirements in light-based communication systems. In addition, the proximity and alignment of transmitter and external receiver may affect signal power requirements.

The type of information that is to be transmitted must also be considered. Information may be transmitted in a weak signal by making it highly redundant, but this will decrease the rate at which information may be acquired.

With certain variables of physiological interest, it may be necessary to monitor baseline of slow variations to observe long-term trends and also to monitor more rapid dynamic changes of interest for diagnostic purposes.

Past designs which use a transmitter power level based on a worst-case analysis of the above factors have a shorter lifetime than necessary.

The present invention provides a method whereby implant transmitter power is controlled externally, based upon the time resolution desired. Thus, the methodology of the invention maximizes the working lifetime of the implants and/or allows a reduction of size for the implanted device. These benefits of the present invention will extend the range of practicality to include implants which heretofore have not been justifiable.

SUMMARY OF THE INVENTION

The method and apparatus of the invention consist of an external apparatus controlled by an operator and an internal implanted apparatus which responds to the external unit by transmitting a signal derived from an internal condition such that the external apparatus receives the signal with the desired clarity.

BRIEF DESCRIPTION OF THE DRAWING

The FIGURE is a block diagram of the preferred embodiment of the present invention.

DETAILED DESCRIPTION OF THE PREFERRED EMBODIMENT

In the embodiment illustrated in the FIGURE, the external part of the system transmits a modulated infrared light signal to the implant by means of a voltage-to-current converter (21) driving a light emitting diode (22). The frequency of this externally transmitted signal is variable within a predetermined range.

The implant detects this light signal via a photodiode (1) which converts the externally transmitted light signal to a current signal which is transformed into a voltage signal by a current-to-voltage converter (2). The resulting voltage signal (a) is applied to a band-pass filter (3). The range of frequencies that the filter will pass is matched to the range of the external transmitter. The output of the filter (b) which is a replica of external signal (1) is applied to a frequency-to-voltage converter (4). One such type converter is known in the art as a so-called phase-locked-loop (PLL) demodulator which is used in this embodiment. The frequency range to which the PLL will respond is matched to that of the external transmitter. The PLL produces two output signals, one (c) indicating the presence of a received signal in the correct range which controls a transistor (5) which in turn switches power from battery (6) to the remaining internal circuitry (7-11). Thus the bulk of the internal circuitry consumes power only when the external apparatus requests implant activation. The other signal (d) is a voltage proportional to the specific frequency of the received signal (b). This level signal (d) is used to determine the voltage which will be applied to voltage-to-current converter (11).

The implant sensor (8) and signal conditioning circuity (9) produce a voltage signal (e) proportional to the physiological variable the implant is designed to measure. This voltage signal (e) is applied to a voltage-to-frequency converter (10) which converts the voltage signal (e) to a frequency-modulated on-off signal (f) whose frequency is in a range that is separated from that of the external transmitter by at least a factor of two. This signal (f) controls the switching of electronic switch (7) to produce a voltage signal (g) at the same frequency as that of the switching signal (f) but whose amplitude is governed by the received external light signal as described above (derived signal d). This sensor-dependent frequency and externally derived amplitude signal (g) is applied to a voltage-to-current converter (11) to drive the implant phototransmitter light-emitting diode (12).

The external photoreceiver (13-14) converts the received internal transmitter light signal to a voltage signal which is then filtered by band-pass filter (15) to remove frequency components outside that of the implant transmitter. This signal (h) is then directed along two different paths.

On one path, signal (h) is applied to rectifier (16) and low pass filter (17) to produce signal (i), the amplitude of which is proportional to the received light-signal average peak-to-peak amplitude. This signal (i) is applied to one input of a differencing or error amplifier (19), the other input of which (j) is supplied by an operator resolution control (18). The output of differencing amplifier (19) is error signal (k) which is proportional to the difference between the desired implant transmitter signal amplitude as set by control (18) and the externally received amplitude as measured by signal (i). This error signal (k) is applied to the external apparatus' voltage-to-frequency converter (20) and phototransmitter (21-22) in such a manner as to cause the external transmitter frequency signal to vary such that the implant transmitter power will be varied by means described above to reduce the error.

The other path of signal (h) is to a phase-locked-loop demodulator (23), the output of which (signal m) is a voltage proportional to the frequency of the externally received implant light signal. The quality of signal-to-noise ratio of this demodulated signal (m) depends upon the quality of the received signal. Thus, at low implant transmitter power levels, the demodulated received signal (m) will be noisier than at higher implant power levels. The demodulated signal (m) is applied to a variable low pass filter (24) to remove noise which may be present in signal (m). At low implant power levels filter (24) may be adjusted by operator control (25) to pass to the output (signal n) only very low frequencies so that random noise in signal (m) would not appear in the output (n). However, this also requires that higher speed dynamic components of the signal (m) which are real and not noise would be lost.

If the operator, by means of control (18), sets desired implant power level to a greater value, filter (24) can be set to pass higher frequencies which may be detected with the subsequent increase in received signal-to-noise ratio.

Not shown in the embodiment represented in the FIGURE is a method of monitoring implant transmitter power. The output of external voltage controlled oscillator (20), signal (1), indirectly controls implant transmitter power. The frequency of this signal (1) can be monitored by devices known in the art to indicate implant transmitter power at any moment in time. This can be used in adjusting the location of the external receiver over the implant transmitter for greater efficiency. Also recording this frequency as a function of time can be used to accumulate knowledge of total implant power expended and to predict remaining implant lifetime.

It is understood that various other modifications will be apparent to, and readily be made by, those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof, by those skilled in the art to which this invention pertains.

What is claimed is:

1. A method for bidirectionally transmitting information between an infrared transmitter implanted in the interior of a living organism, and an external apparatus controlled by an operator, comprising:
   transmitting an infrared light signal at a desired adjustable frequency within a given frequency range from said external apparatus to an infrared light detector implanted in the interior of said organism;
   detecting the frequency of the infrared signal received by the implanted infrared light detector;
   in response to detection of a frequency of the received said infrared signal which is within said given frequency range, converting the detected received frequency within said given frequency range to a voltage signal whose amplitude is proportional to the received frequency;
   measuring a physiological variable of the organism, by means of a sensor implanted in the interior of said organism, and providing a signal whose frequency is proportional to the measured physiological variable;
   frequency modulating said voltage signal with said signal whose frequency is proportional to the measured physiological variable;
   feeding said frequency modulated signal to said transmitter to cause same to transmit a frequency modulated infrared signal to said external apparatus;
   receiving said frequency modulated infrared signal in said external apparatus; and
   detecting the frequency of the received frequency modulated signal as a measure of the physiological variable measured by the sensor.

2. A method as defined in claim 1 further comprising: additionally detecting the amplitude of said received frequency modulated signal as a measure of the transmitted power of said transmitter; and
   adjusting the frequency of the infrared signal transmitted from said external apparatus to control the transmitted power of asid transmitter.

3. A method as defined claim 2 wherein said sensor is normally not activated, and further comprising: in response to detection of a frequency of said received infrared signal which is within said given frequency range, additionally activating said sensor by connecting a battery implanted in the interior of said organism to said sensor to supply power to same.

4. A method as defined in claim 1 wherein said sensor is normally not activated, and further comprising: in response to detection of a frequency of said received infrared signal which is within said given frequency range, additionally activating said sensor by connecting a battery implanted in the interior of said organism to said sensor to supply power to same.

5. A bidirectional data transmission system comprising a first apparatus portion adapted to be implanted within a living organism and a second external apparatus portion controllable by an operator; and wherein:
   said first apparatus portion includes first means for receiving a transmitted signal from said external apparatus portion, second means, connected to the output of said first means, for detecting the frequency of the received signal and for producing a first output signal when the detected frequency of said received signal is within a given frequency range and a second output signal whose amplitude level is proportional to the received frequency, third means for sensing a physiological variable of said living organism and for providing an output signal whose frequency is proportional to the sensed variable, fourth means for modulating said second output signal from said second means with said output signal from said third means to provide a frequency modulated output signal, fifth means, connected to the output of said fourth means, for transmitting said frequency modulated output signal to said external apparatus, a source of power normally connected to said first and second means, and circuit means, responsive to said first output signal from said second means, for connecting said source of power to said third, fourth and fifth means; and, said external apparatus portion includes sixth means for receiving the frequency modulated output signal transmitted by said fifth means, seventh means, connected to the output of said sixth means, for frequency demodulating the received said frequency modulated signal to provide a measure of said physiological variable, eighth means, connected to the output of said sixth means, for producing an output signal proportional to the amplitude of the received frequency modulated signal, ninth means for producing and transmitting an output signal of an adjustable frequency within said given frequency range, and tenth means, responsive to said output signal from said eighth means and to an adjustable value settable by an operator, for adjusting the output frequency of said output signal from said ninth means so as to reduce any differences between said output signals from said eighth means and said adjustable value.

6. A bidirectional data transmission system as defined in claim 5 wherein: said fifth and said ninth means each include a respective infrared signal transmitting device; and said first and sixth means each include a respective infrared light receiving device.

7. A bidirectional data transmission system as defined in claim 5 wherein an adjustable low pass filter is connected to receive the demodulated output signal of said seventh means; said eighth means includes the series connection of a rectifier and a low pass filter; said ninth means includes a voltage controlled oscillator having its output connected to an infrared light emitting semiconductor device for controlling the output of same; and said tenth means comprises a difference amplifier having its output connected to control the output frequency of said oscillator and its two inputs connected respectively to the output of said low pass filter of said eighth means and to a potentiometer for supplying said variable value.

* * * * *